United States Patent
Rodgers et al.

(10) Patent No.: US 9,844,578 B2
(45) Date of Patent: Dec. 19, 2017

(54) ACCELERATED HEALING OF EYE INJURIES BY ANGIOTENSIN PEPTIDES

(71) Applicant: UNIVERSITY OF SOUTHERN CALIFORNIA, Los Angeles, CA (US)

(72) Inventors: Kathleen E. Rodgers, Long Beach, CA (US); Gere S. Dizerega, San Luis Obispo, CA (US); Mark Humayun, Glendale, CA (US); Stan Louie, Fullerton, CA (US); Walid Fouad Ahmed Abdallah, Alhambra, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/784,251

(22) PCT Filed: Apr. 30, 2014

(86) PCT No.: PCT/US2014/036128
§ 371 (c)(1),
(2) Date: Oct. 13, 2015

(87) PCT Pub. No.: WO2014/179440
PCT Pub. Date: Nov. 6, 2014

(65) Prior Publication Data
US 2016/0051622 A1      Feb. 25, 2016

Related U.S. Application Data

(60) Provisional application No. 61/817,596, filed on Apr. 30, 2013, provisional application No. 61/938,851, filed on Feb. 12, 2014.

(51) Int. Cl.
*A61K 38/00* (2006.01)
*A61K 38/08* (2006.01)
*A61K 9/00* (2006.01)
*A61K 45/06* (2006.01)
*A61K 47/38* (2006.01)

(52) U.S. Cl.
CPC .......... *A61K 38/085* (2013.01); *A61K 9/0048* (2013.01); *A61K 9/0051* (2013.01); *A61K 45/06* (2013.01); *A61K 47/38* (2013.01)

(58) Field of Classification Search
None
See application file for complete search history.

(56) References Cited

U.S. PATENT DOCUMENTS 5,036,048 A      7/1991   Watkins et al.

FOREIGN PATENT DOCUMENTS

WO      99/31125 A1      6/1999

OTHER PUBLICATIONS

Mizoue, et al. 2006, Current Eye Research. 31:129-136.*
Mordwinkin, et al., "Toxicological and toxicokinetic analysis of angiotensin (1-7) in two species," Journal pf Pharmaceutical Sciences, 101(1): 373-380, Jan. 2012.
Rodgers, et al., "Effect of NorLeu3-A(1-7) on scar formation over time after full-thickness incision injury in the rat," Wound Repair and Regeneration, Mosby-Year Book, St. Louis, MO 13(3): 309-317, May 2005.
International Search Report PCT/US2014/036128, dated Jul. 25, 2014.

* cited by examiner

*Primary Examiner* — Shulamith H Shafer
(74) *Attorney, Agent, or Firm* — McDonnell Boehnen Hulbert & Berghoff LLP

(57) ABSTRACT

Disclosed herein are methods for treating eye injuries by administering one or more angiotensin peptides to a subject with an eye injury.

17 Claims, 2 Drawing Sheets

A　　　B　　　C

SEQUENCE LISTING

```
<160> NUMBER OF SEQ ID NOS: 51

<210> SEQ ID NO 1
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Asp, Glu, Asn, Ala, Me2Gly, Pro, Glu
      (NH2), Gly, Asp(NH2), or is absent,
<220> FEATURE:
<221> NAME/KEY: MISC_FEATURE
<222> LOCATION: (1)..(1)
<223> OTHER INFORMATION: optional N-terminal Bet, H, Acpc, or Suc
<220> FEATURE:
<221> NAME/KEY: MISC_FEATURE
<222> LOCATION: (2)..(2)
<223> OTHER INFORMATION: Xaa is Arg, Lys, Ala, Cit, Orn, Ser(Ac), Sar,
      D-Arg or D-Lys
<220> FEATURE:
<221> NAME/KEY: MISC_FEATURE
<222> LOCATION: (3)..(3)
<223> OTHER INFORMATION: Xaa is Val, Ala, Leu, norLeu, Ile, Gly, Lys,
      Pro, or Tyr
<220> FEATURE:
<221> NAME/KEY: MISC_FEATURE
<222> LOCATION: (3)..(3)
<223> OTHER INFORMATION: optional C-terminal Aib or Acpc
<220> FEATURE:
<221> NAME/KEY: MISC_FEATURE
<222> LOCATION: (4)..(4)
<223> OTHER INFORMATION: Xaa is Tyr, Tyr(PO3)2, Thr, Ser, homoSer,
      azaTyr, or Ala
<220> FEATURE:
<221> NAME/KEY: MISC_FEATURE
<222> LOCATION: (5)..(5)
<223> OTHER INFORMATION: Xaa is Ile, Ala, Leu, norLeu, Val or Gly
<220> FEATURE:
<221> NAME/KEY: MISC_FEATURE
<222> LOCATION: (6)..(6)
<223> OTHER INFORMATION: Xaa is His, Arg or 6-NH2-Phe
<220> FEATURE:
<221> NAME/KEY: MISC_FEATURE
```

```
<222> LOCATION: (7)..(7)
<223> OTHER INFORMATION: Xaa is Pro or Ala
<220> FEATURE:
<221> NAME/KEY: MISC_FEATURE
<222> LOCATION: (8)..(8)
<223> OTHER INFORMATION: Xaa is Phe, Phe(Br), Ile and Tyr, excluding
      sequences including R4 as a terminal Tyr group

<400> SEQUENCE: 1

Xaa Xaa Xaa Xaa Xaa Xaa Xaa Xaa
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Arg Val Tyr Ile His Pro Phe
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Val Tyr Ile His Pro Phe
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic

<400> SEQUENCE: 4

Asp Arg Val Tyr Ile His Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

Arg Val Tyr Ile His Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Val Tyr Ile His Pro
1               5
```

```
<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Ile His Pro Phe
1

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Asp Arg Val Tyr Ile His
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Asp Arg Val Tyr Ile
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic

<400> SEQUENCE: 10

Asp Arg Val Tyr
1

<210> SEQ ID NO 11
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Nle

<400> SEQUENCE: 11

Arg Leu Tyr Ile His Pro Phe
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Nle
```

```
<400> SEQUENCE: 12

Arg Val Tyr Leu His Pro Phe
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic

<400> SEQUENCE: 13

Asp Arg Pro Tyr Ile His Pro Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 14

Asp Arg Leu Tyr Ile His Pro
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Asp, Glu or absent
<220> FEATURE:
<221> NAME/KEY: MISC_FEATURE
<222> LOCATION: (2)..(2)
<223> OTHER INFORMATION: Xaa is Arg, Lys, or Ala
<220> FEATURE:
<221> NAME/KEY: MISC_FEATURE
<222> LOCATION: (3)..(3)
<223> OTHER INFORMATION: Xaa is Val, Ala, Leu, norLeu, Ile, Gly, Lys,
      or Pro
<220> FEATURE:
<221> NAME/KEY: MISC_FEATURE
<222> LOCATION: (4)..(4)
<223> OTHER INFORMATION: Xaa is Tyr or homoSer
<220> FEATURE:
<221> NAME/KEY: MISC_FEATURE
<222> LOCATION: (5)..(5)
<223> OTHER INFORMATION: Xaa is Ile, Ala, Leu, norLeu, Val or Gly
<220> FEATURE:
<221> NAME/KEY: MISC_FEATURE
<222> LOCATION: (6)..(6)
<223> OTHER INFORMATION: Xaa is His or Arg
<220> FEATURE:
<221> NAME/KEY: MISC_FEATURE
<222> LOCATION: (7)..(7)
<223> OTHER INFORMATION: Xaa is Pro or Ala
<220> FEATURE:
<221> NAME/KEY: MISC_FEATURE
<222> LOCATION: (8)..(8)
<223> OTHER INFORMATION: Xaa is Phe, Ile or is absent

<400> SEQUENCE: 15
```

```
Xaa Xaa Xaa Xaa Xaa Xaa Xaa Xaa
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 16

Asp Arg Leu Tyr Ile
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 17

Asp Arg Leu Tyr Ile His
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Asp Arg Val Tyr Val His Pro Phe
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Asn Arg Val Tyr Val His Pro Phe
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Ala Pro Gly Asp Arg Ile Tyr Val His Pro Phe
1               5                   10

<210> SEQ ID NO 21
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 21

Glu Arg Val Tyr Ile His Pro Phe
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Asp Lys Val Tyr Ile His Pro Phe
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic

<400> SEQUENCE: 23

Asp Arg Ala Tyr Ile His Pro Phe
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic

<400> SEQUENCE: 24

Asp Arg Val Thr Ile His Pro Phe
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Asp Arg Val Tyr Leu His Pro Phe
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Asp Arg Val Tyr Ile Arg Pro Phe
1               5

<210> SEQ ID NO 27
<211> LENGTH: 8
<212> TYPE: PRT
```

```
<213> ORGANISM: Artificial Sequence
<220> FEATURE:
<223> OTHER INFORMATION: Synthetic

<400> SEQUENCE: 27

Asp Arg Val Tyr Ile His Ala Phe
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic

<400> SEQUENCE: 28

Asp Arg Val Tyr Ile His Pro Tyr
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Pro Arg Val Tyr Ile His Pro Phe
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Tyr is Try(PO3)2

<400> SEQUENCE: 30

Asp Arg Val Tyr Ile His Pro Phe
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 31

Asp Arg Leu Tyr Ile His Pro Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
```

```
<223> OTHER INFORMATION: Nle

<400> SEQUENCE: 32

Asp Arg Val Tyr Leu His Pro Phe
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: homoSer

<400> SEQUENCE: 33

Asp Arg Val Ser Tyr Ile His Pro Phe
1               5

<210> SEQ ID NO 34
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is H, Arg, Lys, Ala, Orn, Citron, Ser(Ac),
      Sar, D-Arg or D-Lys
<220> FEATURE:
<221> NAME/KEY: MISC_FEATURE
<222> LOCATION: (2)..(2)
<223> OTHER INFORMATION: Xaa is Val, Ala, Leu, norLeu, Ile, Gly, Lys,
      Pro, or Tyr
<220> FEATURE:
<221> NAME/KEY: MISC_FEATURE
<222> LOCATION: (2)..(2)
<223> OTHER INFORMATION: optional C-terminal Acpc or Aib
<220> FEATURE:
<221> NAME/KEY: MISC_FEATURE
<222> LOCATION: (3)..(3)
<223> OTHER INFORMATION: Xaa is Tyr, Tyr(PO3)2, Thr, Ser, homoSer,
      azaTyr, or Ala
<220> FEATURE:
<221> NAME/KEY: MISC_FEATURE
<222> LOCATION: (4)..(4)
<223> OTHER INFORMATION: Xaa is Ile, Ala, Leu, norLeu, Val or Gly
<220> FEATURE:
<221> NAME/KEY: MISC_FEATURE
<222> LOCATION: (5)..(5)
<223> OTHER INFORMATION: Xaa is His, Arg or 6-NH2-Phe
<220> FEATURE:
<221> NAME/KEY: MISC_FEATURE
<222> LOCATION: (6)..(6)
<223> OTHER INFORMATION: Xaa is Pro or Ala
<220> FEATURE:
<221> NAME/KEY: MISC_FEATURE
<222> LOCATION: (7)..(7)
<223> OTHER INFORMATION: Xaa is Phe, Phe(Br), Ile or Tyr, excluding
      sequences including R4 as a terminal Tyr group

<400> SEQUENCE: 34

Xaa Xaa Xaa Xaa Xaa Xaa Xaa
1               5

<210> SEQ ID NO 35
<211> LENGTH: 7
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (1)..(1)
<223> OTHER INFORMATION: Xaa is Arg, Lys, Ala, Cit, Orn, Ser(Ac), Sar,
      D-Arg or D-Lys
<220> FEATURE:
<221> NAME/KEY: MISC_FEATURE
<222> LOCATION: (2)..(2)
<223> OTHER INFORMATION: optional C-terminal Aib or Acpc
<220> FEATURE:
<221> NAME/KEY: MISC_FEATURE
<222> LOCATION: (2)..(2)
<223> OTHER INFORMATION: Xaa is Val, Ala, Leu, norLeu, Ile, Gly, Lys,
      Pro, or Tyr
<220> FEATURE:
<221> NAME/KEY: MISC_FEATURE
<222> LOCATION: (4)..(4)
<223> OTHER INFORMATION: Xaa is Ile, Ala, Leu, norLeu, Val or Gly

<400> SEQUENCE: 35

Xaa Xaa Tyr Xaa His Pro Phe
1               5

<210> SEQ ID NO 36
<211> LENGTH: 7
<212> TYPE: PRT
<213> ORGANISM: Artificial Sequence
<220> FEATURE:
<223> OTHER INFORMATION: Synthetic

<400> SEQUENCE: 36

Arg Val Tyr Gly His Pro Phe
1               5

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

Arg Val Tyr Ala His Pro Phe
1               5

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Asp Arg Val Ala Ile His Pro
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic

<400> SEQUENCE: 39

Asp Arg Pro Tyr Ile His Pro
1               5

<210> SEQ ID NO 40
```

```
<211> LENGTH: 7
<212> TYPE: PRT
<213> ORGANISM: Artificial Sequence
<220> FEATURE:
<223> OTHER INFORMATION: Synthetic

<400> SEQUENCE: 40

Asp Arg Lys Tyr Ile His Pro
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Nle

<400> SEQUENCE: 41

Asp Arg Leu Tyr Ile His Pro
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Asp Arg Val Tyr Ile His Pro Ile
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Arg Val Ala Ile His Pro Phe
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Arg Val Ala Ile His Pro Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic

<400> SEQUENCE: 45

Gly Arg Val Tyr Ile His Pro Phe
1               5
```

```
<210> SEQ ID NO 46
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Nle

<400> SEQUENCE: 46

Arg Val Tyr Leu His Pro Phe
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: C-terminal 1-aminocyclopentane carboxylic acid

<400> SEQUENCE: 47

Asp Arg Tyr Ile His Pro Phe
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Orn

<400> SEQUENCE: 48

Asp Xaa Val Tyr Ile His Pro Phe
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: C-terminal Citron

<400> SEQUENCE: 49

Asp Val Tyr Ile His Pro Phe
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50
```

```
Asp Arg Pro Ala Ile His Pro
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: 3Hyp

<400> SEQUENCE: 51

Asp Arg Pro Ala Ile His Pro
1               5
```

ACCELERATED HEALING OF EYE INJURIES BY ANGIOTENSIN PEPTIDES

CROSS REFERENCE

This application is a U.S. National Phase of International Application No. PCT/US2014/036128, filed Apr. 30, 2014, which claims priority to U.S. Provisional Patent Application No. 61/817,596, filed Apr. 30, 2013 and U.S. Provisional Patent No. 61/938,851, filed Feb. 12, 2014, the disclosures of which are hereby incorporated by reference in their entireties.

BACKGROUND

Eye injury can occur as a result of a variety of insults, including surgical interventions chemical exposure, trauma, infections or via foreign body injury to the eye. These injuries are very slow to heal, if they heal at all and the continuing injury is a portal for infection and other contamination that can lead to loss of visual acuity or blindness.

SUMMARY OF THE INVENTION

In a first aspect, the invention provides methods for treating an eye injury, comprising administering to a subject with an eye injury an amount effective of an angiotensin peptide to treat the eye injury. In one embodiment, the eye injury is caused by trauma, light/radiation or chemical exposure, disease, or a surgical procedure. In another embodiment, the eye injury comprises an injury selected from the group consisting of post-surgical inflammation, postoperative fibrosis, a post-surgical increase in intra-ocular pressure, a corneal injury, a cataract incision, laser-assisted in situ keratomilensis (LASIK) wounds, dry eye, and a photorefractive keratectomy (PRK) wound.

In a further embodiment the eye injury is a corneal injury, wherein the conical injury comprises penetration of the corneal epithelium, corneal endothelium, corneal Bowman's membrane, Descemet's membrane and/or anterior part of the corneal stroma. In another embodiment, the corneal injury comprises a corneal abrasion or corneal laceration. In further embodiment, the treating comprises reducing development and/of severity of a symptom selected from the group consisting of fibrosis, inflammation, edema, increases in intraocular pressure, eye pain, increased tearing compared to normal, blurred vision, sensitivity to light, altered visual acuity, and a sensation of something being stuck in the eye. In another embodiment, the treating comprises reduced time to corneal healing and/or anterior chamber formation compared to control.

In one embodiment, the eye injury comprises dry eye. In another embodiment, the treating comprises reducing development and/or severity of a symptom selected from the group consisting of eye irritation, stinging, redness, grittiness, scratchiness, burning, conjunctival discharge, a feeling of something in the eyes, excess watering, and blurred vision.

In a further embodiment, the eye injury results from ocular surgery. In various embodiments, the ocular surgery is selected from the group consisting of keratomilensis laser-assisted in situ keratomilensis (LASIK), automated lamellar keratoplasty (ALK), laser assisted sub-epithelial keratomilensis (LASEK), photorefractive keratectomy (PRK), laser thermal keratoplasty (LTX), conductive keratoplasty (CK), limbal relaxing incisions (LRI), astigmatic keratotomy (AK), radial keratotomy (RK), mini-asymmetric radial keratotomy (M.A.R.K.), hexagonal keratotomy (HK), implantable contact lenses, presbyopia reversal, anterior ciliary sclerotomy (ACS), laser reversal of presbyopia (LRP), scleral expansion bands, the Karmra inlay, scleral reinforcement surgery, corneal transplant surgery, penetrating keratoplasty (PK), keratoprosthesis implantation (KPro), cataract surgery, insertion of intra-ocular lenses, phototherapeutic keratectomy (PIK), pterygium excision, corneal tattooing, vitrectomy, pan retinal photocoagulation (PRP), retinal detachment repair, laser photocoagulation, pneumatic retinopexy, retinal cryopexy, macular hole repair, partial lamellar sclerouvectomy, partial lamellar sclerocyclochoroidectomy, partial lamellar sclerochoroidectomy, posterior sclerotomy, radial optic neurotomy, macular translocation surgery, eye muscle surgery, oculoplastic surgery, and surgery to treat cataracts, glaucoma and diabetic retinopathy.

In another embodiment, the treating comprises reducing development and/or severity of a symptom selected from the group consisting of postoperative fibrosis, postoperative inflammation, postoperative increases in intraocular pressure, lacerations, conjunctival discharge, punctures, eye pain, increased tearing compared to normal, blurred vision sensitivity to light, altered visual acuity, and a sensation of something being stuck in the eye.

In one embodiment, the angiotensin peptide comprises or consists of Nle3 A(1-7) (SEQ ID NO: 14). In another embodiment, the angiotensin peptide is administered at a concentration of about 0.01 to about 1% on a weight (mg)/volume (ml) basis, or on a weight/weight (mg) basis, or at a concentration of about 0.03% to about 0.3% on a weight (mg)/volume (ml) basis, or on a weight/weight (mg) basis. In a further embodiment, the angiotensin peptide is administered in a topical formulation. In various embodiments, the topical formulation is selected from the group consisting of hydrogels, creams, viscoelastics ointments, pastes, drops, nanoparticles, polymeric-based formulations and lotions. In another embodiment, the formulation is administered via a delivery aid selected from the group consisting of a bandage contact lens, contact lens, formix-based implant, eye patch or patched eye, pressure patch, and eye shield. In a further embodiment, the topical formulation comprises about 0.5% to about 4% (or about 1% to about 3%) hydroxyethyl cellulose (HEC) on a weight (mg)/volume (ml) basis, or on a weight/weight (mg) basis.

In a further embodiment, the method further comprises administering to the subject an amount effective to treat an eye injury of an active agent selected from the group consisting of artificial tears, antibiotics, antivirals, antifungals, analgesics, and anti-inflammatory drugs.

In a second aspect, the invention provides pharmaceutical compositions, comprising:

(a) an angiotension peptide;

(b) an active agent selected from the group consisting of artificial tears, antibiotics, antivirals, antifungals, analgesics, and anti-inflammatory drugs; and (c) a pharmaceutically acceptable carrier.

In one embodiment, the active agent comprises artificial tears. In another embodiment, the angiotensin peptide comprises or consists of Nle3 A(1-7) (SEQ ID NO: 14). In a further embodiment, the angiotensin peptide is administered at a concentration of about 0.01% to about 1% (or about 0.03% to about 0.3%) on a weight (mg)/volume (ml) basis, or on a weight/weight (mg) basis.

In another embodiment, the pharmaceutical composition is provided as a topical formulation. In one embodiment, the topical formulation is selected from the group consisting of hydrogels, creams, viscoelastics, ointments, pastes, drops, nanoparticles, polymeric-based formulations and lotions. In a further embodiment, the topical formulation is provided on a delivery aid selected from the group consisting of a bandage contact lens, contact lens, formix-based implant, eye patch or patched eye, pressure patch, and eye shield. In another embodiment, the topical formulation comprises about 0.5% to about 4% (or about 1% to about 3%) hydroxyethyl cellulose (HEC) on a weight (mg)/volume (ml) basis, or on a weight/weight (mg) basis.

DETAILED DESCRIPTION OF THE INVENTION

Figure 1:
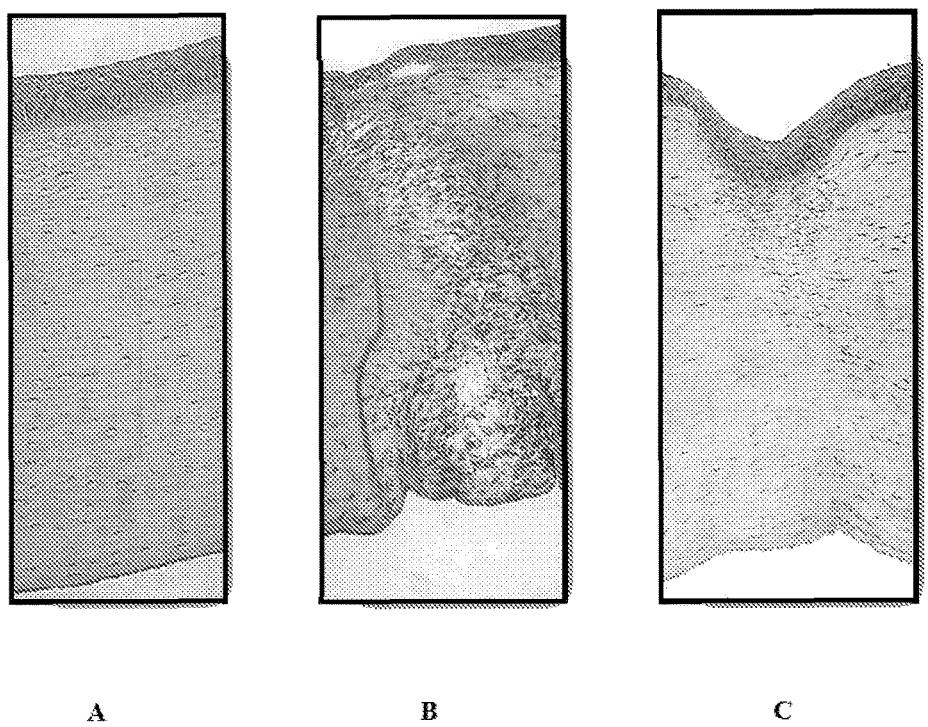
FIG. 1. Hematoxylin and eosin staining of the corneal incision site showed normalized architecture with reduced fibrosis with active treatment using Nle3-A(1-7) (panel C) compared to vehicle control (Panel B). A no incision control is shown in Panel A.

As used herein, the singular forms "a," "an" and "the" include plural referents unless the context clearly dictates otherwise. "And" as used herein is interchangeably used with "of" unless expressly stated otherwise.

All embodiments within and between different aspects of the invention can be combined unless the context clearly dictates otherwise.

As used herein, the term "about" means+/−5% of the relevant measurement or unit.

In a first aspect, the present invention provides methods for treating an eye injury, comprising administering to a subject with an eye injury an amount effective of an angiotensin peptide to treat the eye injury.

The inventors have discovered that angiotensin peptides (as defined below) can be used to treat a variety of eye injuries to heal the injury with limited or no opacification of the cornea. Currently the only modalities under development to close injuries to the eye are sutures, adhesives or glues. These do not promote healing and are no longer effective once the device is removed.

While not being bound by any mechanism of action, the inventors believe that the methods of the invention promote avascular healing of eye injuries, which is unexpected to those of skill in the art, since tissue injury healing has always been associated with a vascular healing process (i.e., mediated by red and white blood cells as well as endothelial or vascular channels.) The methods of the present invention accelerate eye healing without neovascularization or distortion of vision, and reduce inflammation and edema.

The subject may be any subject that has suffered an eye injury, including but not limited to humans or other primates, goats, dogs, cats, horses, cattle, sheep, pigs, and other mammals.

As used herein, an "eye injury" is any injury to the eye that results in damage to the eye that could lead to reduced visual acuity or opacification of the cornea, inflammation and/or delayed healing. The methods may be used with any such eye injury, including but not limited to lacerations of eye tissue, penetrations of eye tissue, postoperative inflammation, postoperative fibrosis, a postoperative increase in intra-ocular pressure, a corneal injury, a cataract incision, corneal opacification, laser-assisted hi situ keratomilensis (LASIK) wounds, a photorefractive keratectomy (PRK) wound, radiation or chemical exposure, corneal transplantation, dry eye, or eye infection.

The eye injuries may be caused by any means. Including but not limited to surgical procedures, trauma (airborne sand, glass, wood, sand, dirt, military projectiles, metal, stone, or other materials; high speed objects such as baseballs, tennis balls, fists, BBs, firecrackers, etc.), chemical or radiation exposure, infection, ulceration, keratoconjunctivitis sicca (KCS), disease, autoimmune disorders, aging, and/or inflammation.

In another embodiment, the eye injury comprises a corneal injury. As used herein, a "corneal injury" means any injury to the cornea. The cornea is the transparent tissue covering the front of the eye. It works with the lens of the eye to focus images on the retina. Any conical injury can be treated by the methods of the invention, including but not limited to conical injuries comprising penetration of the corneal epithelium, corneal Bowman's membrane, corneal endothelium. Descemet's membrane and/or anterior part of the corneal stroma. Conical healing is important, not only to reestablish the protective epithelium, but also for the restoration of corneal transparency and clear vision. The corneal healing response depends on various factors including the type, size, and extent of the injury; the nature of the injuring agent; the status of the eye; and the general status of the subject. The most common conical injuries involve superficial penetration of the epithelium including incisions and excisions as well as abrasions. Bowman's membrane, and the anterior part of the stroma. Superficial corneal defects may be associated with trauma or diseases, such as dystrophies, neurotrophic, toxic, or infective keratitis including bacterial fungal, or viral, but also follow surgical procedures such as epithelial debridement, phototherapeutic keratectomy, photorefractive keratectomy, or laser in situ keratomilensis. Due to its exposed site and sheerness corneal surface injuries are the most common ophthalmic complaint and recurrent erosions develop in a sub-population of patients with surface injuries as well as with individuals with alterations in the stem cells located in the limbus.

In another exemplary embodiment, the corneal injury comprises a corneal abrasion or a corneal laceration. The corneal abrasion or laceration may result from any cause, including but not limited to chemical irritation, overuse of contact lenses or use of poorly fitting contact lenses, scratches, foreign object in the eye, infection, or light-based corneal abrasions (sunlight, sun lamps, snow or water reflection of light, arc-welding, etc.).

Corneal injury can occur as a result of surgical interventions or via foreign body injury to the eye. This injuries are very slow to heal, if they heal at allow and the continuing injury is a port to infection and other contamination that can lead to reduced visual acuity and/or blindness In one embodiment, the eye injury is caused by ocular surgery. The method may be used to treat an eye injury resulting from any ocular surgery, including but not limited to refractive surgery (including but not limited to keratomilensis, laser-assisted hi situ keratomilensis (LARK), automated lamellar keratoplasty (ALK), laser assisted sub-epithelial keratomilensis (LASEK), photorefractive keratectomy (PRK), laser thermal keratoplasty (LTK), conductive keratoplasty (CK), limbal relaxing incisions (LIU), astigmatic, keratotomy (AK), radial keratotomy (RK), mini-asymmetric radial keratotomy (M.A.R.K.), hexagonal keratotomy (HK), implantable contact lenses, presbyopia reversal, anterior ciliary sclerotomy (ACS), laser reversal of presbyopia (LRP), scleral expansion bands, the Karmra inlay, and scleral reinforcement surgery); conical surgery (including but not limited to the refractive surgeries above and corneal transplant surgery, penetrating keratoplasty (PK), keratoprosthesis implantation (KPro), cataract surgery, insertion of intra-ocular lenses, phototherapeutic, keratectomy (PTK), pterygium excision, and corneal tattooing); vitreo-retinal surgery (including but not limited to vitrectomy, pan retinal photocoagulation (PRP), retinal detachment repair, laser photocoagulation, pneumatic retinopexy, retinal cryopexy macular hole repair, partial lamellar sclerouvectomy partial lamellar sclerocyclochoroidectomy, partial lamellar sclerochoroidectomy, posterior sclerotomy, radial optic neurotomy and macular translocation surgery); eye muscle surgery, oculoplastic surgery, and surgery to treat, cataracts, glaucoma, and diabetic, retinopathy.

In another embodiment, the eye injury is dry eye. People with dry eyes may experience symptoms of irritated, stinging, redness, gritty, scratchy, or burning eyes, a feeling of something in their eyes, excess watering, and blurred vision. If left untreated, this condition can lead to pain, ulcers or scaring of the cornea. Dry eyes may be more prone to bacterial infections or inflammation. Advanced dry eyes may damage the front surface of the eye and impair vision. In various embodiments, the dry eye may be the result of surgery, keratoconjunctivitis sicca (KCS), autoimmune disease, aging, and or inflammation, and/or inability to adequately produce tears properly, or when tears are not of correct consistency and evaporate quickly.

In one embodiment, the angiotensin peptides for use in the invention comprise or consist of a sequence of at least four contiguous amino acids of groups $R^1$-$R^8$ in the sequence of general formula I $$R^1\text{-}R^2\text{-}R^3\text{-}R^4\text{-}R^5\text{-}R^6\text{-}R^7\text{-}R^8 \quad \text{(SEQ ID NO: 1)}$$

wherein $R^1$ is selected from the group consisting of H, Asp, Glu, Asn, Acpc, (1-aminocyclopentane carboxylic acid), Ala, Me²Gly, Pro, Bet, Glu(NH₂), Gly, Asp(NH₂) and Suc, or is absent.

$R^2$ is selected from the group consisting of Arg, Lys, Ala, Cit, Orn, Ser(Ac), Sar, D-Arg and D-Lys.

$R^3$ is selected from the group consisting of Val, Ala, Len, norLeu, Ile, Gly, Lys, Pro, Aib, Acpc and Tyr;

$R^4$ is selected from the group consisting of Tyr, Tyr(PO₃)₂, Thr, Ser, homoSer, azaTyr, and Ala:

$R^5$ is selected from the group consisting of Ile, Ala, Len, norLeu, Val and Gly;

$R^6$ is selected from the group consisting of His, Arg or 6-NH₂-Phe;

$R^7$ is selected from the group consisting of Pro or Ala; and $R^8$ is selected from the group consisting of Phe, Phe(Br), Ile and Tyr, excluding sequences including $R^4$ as a terminal Tyr group.

Exemplary AT2 agonists useful in the practice of the invention include the AII analogues set forth above subject to the restriction that $R^8$ is p-NH₂-Phe.

In a further preferred embodiment of each of the above embodiments (SEQ ID NO: 15), $R^1$ is selected from the group consisting of Asp and Gin, or is absent;

$R^2$ is selected from the group consisting of Arg, Lys, and Ala;

$R^3$ is selected from the group consisting of Val, Ala, Len, norLeu, Ile, Gly, Lys, and Pro;

$R^4$ is selected from the group consisting of Tyr and homoSer;

$R^5$ is selected from the group consisting of Ile, Ala, Len, norLeu, Val and Gly;

$R^6$ is selected from the group consisting of His and Arg;

$R^7$ is selected from the group consisting of Pro or Ala; and $R^8$ is selected from the group consisting of Phe, Ile, or is absent.

Other AT2 agonists include those disclosed in Wallinder. C, 2008. Design, Synthesis, and Biological Evaluation of Selective Nonpeptide AT2 Receptor Agonists and Antagonists, Acta Universitatis Upsaliensis, Digital Comprehensive Summaries of Uppsala Dissertations from the Faculty of Pharmacy 78, 96 pp. UPPSALA ISBN 978-91-554-7263-4.

In alternate embodiments, the angiotensin peptides comprise or consist of at least five, six, seven, or eight contiguous amino acids of groups $R^1$-$R^8$ in the sequence of general formula I. In a further alternative, the angiotensin peptides consist essentially of a sequence of at least four, five, six, seven, or eight contiguous amino acids of groups $R^1$-$R^8$ in the sequence of general formula I.

Particularly preferred combinations for $R^1$ and $R^2$ are Asp-Arg, Asp-Lys, Glu-Arg and Glu-Lys. Particularly preferred embodiments of this class include the following: AIII or AII(2-8). Arg-Val-Tyr-Ile-His-Pro-Phe [SEQ ID NO:2]; AII(3-8), also known as des1-AIII or AIV, Val-Try-Ile-His-Pro-Phe [SEQ ID NO:3]; AII(1-7), Asp-Arg-Val-Tyr-ile-His-Pro [SEQ ID NO:4]; AII(2-7). [SEQ ID NO:5]; AII(3-7), Val-Tyr-Ile-His-Pro [SEQ ID NO:6]; AII(5-8), Ile-His-Pro-Phe [SEQ ID NO:7]; AII(1-6), Asp-Arg-Val-Tyr-Ile-His [SEQ ID NO:8]; AII(1-5), Asp-Arg-Val-Tyr-Ile [SEQ. ID NO:9]; AII(1-4), Asp-Arg-Val-Tyr [SEQ ID NO: 10]; and AII(1-3), Asp-Arg-Val. Other preferred embodiments include: Arg-norLeu-Tyr-Ile-His-Pro-Phe [SEQ ID NO:11] and Arg-Val-Tyr-norLeu-His-Pro-Phe [SEQ ID NO: 12]. Still another preferred embodiment encompassed within the scope of the invention is a peptide having the sequence Asp-Arg-Pro-Tyr-Ile-His-Pro-Phe [SEQ ID NO:13].

In another embodiment, the angiotensin peptides for use in the present invention comprise or consists of at least 5 contiguous amino acids of Nle3-A(1-7).

Nle3-A(1-7) is a peptide consisting of the amino acid sequence Asp-Arg-Nle-Tyr-Ile-His-Pro (SEQ ID NO: 14). In various further embodiments, the peptide administered to the subject may be Asp-Arg-Nle-Tyr-Ile (SEQ ID NO: 16), Asp-Arg-Nle-Tyr-Ile-His (SEQ NO: 17), or Asp-Arg-Nle-Tyr-Ile-His-Pro (SEQ ID NO: 14).

Other preferred embodiments comprise or consist of

```
                                         SEQ ID NO: 18
    Asp-Arg-Val-Tyr-Val-His-Pro-Phe

SEQ ID NO: 19
    Asn-Arg-Val-Tyr-Val-His-Pro-Phe

SEQ ID NO: 20
    Ala-Pro-Gly-Asp-Arg-Ile-Tyr-Val-His-Pro-Phe

SEQ ID NO: 21
    Glu-Arg-Val-Tyr-Ile-His-Pro-Phe

SEQ ID NO: 22
    Asp-Lys-Val-Tyr-Ile-His-Pro-Phe

SEQ ID NO: 23
    Asp-Arg-Ala-Tyr-Ile-His-Pro-Phe
```

```
Asp-Arg-Val-Thr-Ile-His-Pro-Phe                   SEQ ID NO: 24

Asp-Arg-Val-Tyr-Leu-His-Pro-Phe                   SEQ ID NO: 25

Asp-Arg-Val-Tyr-Ile-Arg-Pro-Phe                   SEQ ID NO: 26

Asp-Arg-Val-Tyr-Ile-His-Ala-Phe                   SEQ ID NO: 27

Asp-Arg-Val-Tyr-Ile-His-Pro-Tyr                   SEQ ID NO: 28

Pro-Arg-Val-Tyr-Ile-His-Pro-Phe                   SEQ ID NO: 29

Asp-Arg-Pro-Tyr-Ile-His-Pro-Phe                   SEQ ID NO: 13

Asp-Arg-Val-Tyr(PO3)2-Ile-His-Pro-Phe             SEQ ID NO: 30

Asp-Arg-norLeu-Tyr-Ile-His-Pro-Phe                SEQ ID NO: 31

Asp-Arg-Val-Tyr-norLeu-His-Pro-Phe                SEQ ID NO: 32

Asp-Arg-Val-homoSer-Tyr-Ile-His-Pro-Phe           SEQ ID NO: 33
```

Another class of angiotensin peptides of particular interest in accordance with the present invention are those of the general formula II:

$$R^2-R^3-R^4-R^5-R^6-R^7-R^8 \quad \text{(SEQ ID NO: 34)}$$

in which $R^2$ is selected from the group consisting of H, Arg, Lys, Ala, Orn, Citron, Ser(Ac), Sar, D-Arg and D-Lys; $R^3$-$R^8$ are as defined above, and
excluding sequences including $R^4$ as a terminal Tyr group.

A particularly preferred subclass of the compounds of general formula II has the formula:

$$R^2-R^3-\text{Tyr}-R^5-\text{His-Pro-Phe} \quad \text{[SEQ ID NO: 35]}$$

wherein $R^2$, $R^3$ and $R^5$ are as previously defined. Particularly preferred is angiotensin III of the formula Arg-Val-Tyr-Ile-His-Pro-Phe [SEQ ID NO:2]. Other preferred compounds include peptides having the structures Arg-Val-Tyr-Gly-His-Pro-Phe [SEQ ID NO:36] and Arg-Val-Tyr-Ala-His-PID-Phe [SEQ ID NO:37].

In the above formulas, the standard three-letter abbreviations for amino acid residues are employed. Other residues are abbreviated as follows:

TABLE 1

| Abbreviation for Amino Acids | |
|---|---|
| Me²Gly | N,N-dimethylglycyl |
| Bet | 1-carboxy-N,N,N-trimethylmethanaminium hydroxide inner salt (betaine) |
| Suc | Succinyl |
| Phe(Br) | p-bromo-L-phenylalanyl |
| azaTyr | aza-α'-homo-L-tyrosyl |
| Acpc | 1-aminocyclopentane carboxylic acid |
| Aib | 2-aminoisobutyric acid |

TABLE 1-continued

| Abbreviation for Amino Acids | |
|---|---|
| Sar | N-methylglycyl (sarcosine) |
| Cit | Citron |
| Orn | Ornithine |
| NorLeu (Nle) | NorLeucine |
| HomoSer | HomoSerine (isotheronine) |

Analogues of particular include the following:

TABLE 2

Angiotensin II Analogues

| AII Analogue Name | Amino Acid Sequence | Sequence Identifier |
|---|---|---|
| Analogue 1 | Asp-Arg-Val-Tyr-Val-His-Pro-Phe | SEQ ID NO: 18 |
| Analogue 2 | Asn-Arg-Val-Tyr-Val-His-Pro-Phe | SEQ ID NO: 19 |
| Analogue 3 | Ala-Pro-Gly-Asp-Arg-Ile-Tyr-Val-His-Pro-Phe | SEQ ID NO: 20 |
| Analogue 4 | Glu-Arg-Val-Tyr-Ile-His-Pro-Phe | SEQ ID NO: 21 |
| Analogue 5 | Asp-Lys-Val-Tyr-Ile-His-Pro-Phe | SEQ ID NO: 22 |
| Analogue 6 | Asp-Arg-Ala-Tyr-Ile-His-Pro-Phe | SEQ ID NO: 23 |
| Analogue 7 | Asp-Arg-Val-Thr-Ile-His-Pro-Phe | SEQ ID NO: 24 |
| Analogue 8 | Asp-Arg-Val-Tyr-Leu-His-Pro-Phe | SEQ ID NO: 25 |
| Analogue 9 | Asp-Arg-Val-Tyr-Ile-Arg-Pro-Phe | SEQ ID NO: 26 |
| Analogue 10 | Asp-Arg-Val-Tyr-Ile-His-Ala-Phe | SEQ ID NO: 27 |
| Analogue 11 | Asp-Arg-Val-Tyr-Ile-His-Pro-Tyr | SEQ ID NO: 28 |
| Analogue 12 | Pro-Arg-Val-Tyr-Ile-His-Pro-Phe | SEQ ID NO: 29 |
| Analogue 13 | Asp-Arg-Pro-Tyr-Ile-His-Pro-Phe | SEQ ID NO: 13 |
| Analogue 14 | Asp-Arg-Val-Tyr(PO3)2-Ile-His-Pro-Phe | SEQ ID NO: 30 |
| Analogue 15 | Asp-Arg-norLeu-Tyr-Ile-His-Pro-Phe | SEQ ID NO: 31 |
| Analogue 16 | Asp-Arg-Val-Tyr-norLeu-His-Pro-Phe | SEQ ID NO: 32 |
| Analogue 17 | Asp-Arg-Val-homoSer-Tyr-Ile-His-Pro-Phe | SEQ ID NO: 33 |

Other particularly preferred embodiments include:

```
1GD Ala4-AII(1-7)  DRVAIHP          SEQ ID NO: 38

2GD Pro3-AII(1-7)  DRPYIHP          SEQ ID NO: 39
```

-continued

| | | |
|---|---|---|
| 5GD Lys3-AII(1-7) DRKYIHP | SEQ ID NO: 40 | |
| 9GD NorLeu-AII(1-7) DR(nor)YIHP | SEQ ID NO: 41 | |
| GSD 28 Ile$^8$-AII DRVYIHPI | SEQ ID NO: 42 | |
| Ala3aminoPhe6 AII: RVAIHPF | SEQ ID NO: 43 | |
| Ala3-AIII RVAIHPF | SEQ ID NO: 44 | |
| Gly$^1$-AII GRVYIHPF | SEQ ID NO: 45 | |
| NorLeu$^4$-AIII --RVYnLHPF | SEQ ID NO: 46 | |
| Acpc$^3$-AII DR(Acpc)YIHPF | SEQ ID NO: 47 | |
| GSD 37B Orn$^2$-AII D(Orn)VYIHPF | SEQ ID NO: 48 | |
| GSD38B Citron$^2$-AII D(Citron)VYIHPF | SEQ ID NO: 49 | |
| 3GD Pro$^3$Ala$^4$-AII(1-7) DRPAIHP | SEQ ID NO: 50 | |
| 8GD Hydroxy-Pro$^3$-AII(1-7) DRP(OH)AIHP | SEQ ID NO: 51 | |

In another embodiment, the angiotensin peptides may be any of those disclosed in US20100055146, incorporated by reference herein in its entirety. In various embodiments, the polypeptide is:

a 4,7-cyclized analog of Angiotensin II (Ang(1-8), or any of its analogues disclosed herein:

a 4,7-cyclized analog of Angiotensin III (Ang(2-8)), or any of its analogues disclosed herein:

a 4,7-cyclized analog of Angiotensin IV (Ang(3-8)), or any of its analogues disclosed herein; or a 4,7-cyclized analog of Ang(1-7), or any of its analogues disclosed herein.

In another embodiment, the methods comprise administering an agonist of the MAS receptor. Any suitable polypeptide or non-polypeptide agonist of the MAS receptor may be used, including but not limited to A(1-7) and analogues thereof, A779 (D-Ala A(1-7); available from Sigma Chemical Co.) and AVE0991, (see, for example, Pinheiro et al., Hypertension. 2004 October; 44(4):490-6. Epub 2004 Aug. 23).

The angiotensin peptides for use in the present invention may be linear or cyclized in any suitable manner.

The angiotensin peptides may be recombinantly expressed or chemically synthesized using any suitable techniques, which are well within the level of those of skill in the art.

As used herein, "treat" or "treating" the eye injury means accomplishing one or more of the following: (a) reducing the severity of the eye injury; (b) limiting or preventing development of symptoms characteristic of the eye injury being treated; (c) inhibiting worsening of symptoms characteristic of the eye injury being treated; (d) limiting or preventing recurrence of the eye injury in patients that have previously had the disorder(s); and (e) limiting or preventing recurrence of symptoms in patients that were previously symptomatic for the eye injury. For example, depending on the eye injury being treated, symptoms may include postoperative fibrosis, postoperative inflammation, postoperative increases in intraocular pressure, lacerations, punctures, eye pain, increased tearing compared to normal, binned vision, sensitivity to light, altered visual acuity, and/or the sensation of something being stuck in the eye.

The polypeptide may be administered in any suitable dose as determined in light of all relevant factors. In one embodiment of all aspects of the invention, the polypeptide, or salt thereof, is administered in a pharmaceutical formulation at a concentration of about 0.001% to about 3% on a weight (mg)/volume (ml) basis, or on a weight/weight (mg) basis. In various further embodiments, the polypeptide, or salt thereof is administered in a pharmaceutical formulation at a concentration of about 0.005% to about 3%; about 0.01% to about 3%; about 0.05% to about 3%; about 0.01% to about 3%; about 0.5% to about 3%; about 1% to about 3%; about 2% to about 3%; about 0.005% to about 2%; about 0.01% to about 2%; about 0.05% to about 2%; about 0.01% to about 2%; about 0.5% to about 2%; about 1% to about 2%; about 0.005% to about 1%; about 0.01% to about 1%; about 0.05% to about 1%; about 0.01% to about 1%; about 0.5% to about 1%; about 0.005% to about 0.75%; about 0.01% to about 0.75%; about 0.005% to about 0.75%; about 0.01% to about 0.75%; about 0.03% to about 1%; about 0.03% to about 0.75%; about 0.03% to about 0.3%; about 0.03% to about 0.5%; about 0.03% to about 0.25%; about 0.03% to about 0.1%; about 0.03% to about 0.075%; about 0.03% to about 0.05%; and about 0.03% to about 0.3%; or about 0.03% or about 0.3%, all on a weight (mg)/volume (ml) basis, or on a weight/weight (mg) basis.

In all aspects of the invention, the polypeptide or salt thereof may be administered by any suitable route, such as systemic administration (including oral administration); preferably via topical administration, including but not limited to as a drop (i.e.: in suspension, in solution, or as au ointment), with a bandage contact lens, sustained delivery via contact lens, a fornix-based implant or with an eye patch or patched eye. In one embodiment, the methods of the invention can comprise administering a topical formulation as often as deemed appropriate, i.e.: once per day, twice per day, three times per day, four times per day, etc. The methods may further comprise administration of the polypeptide, or salt thereof for as longed as deemed desirable by an attending physician.

In one embodiment of all aspects of the invention, the topical administration comprises administration in a formulation selected from the group consisting of hydrogels, creams, viscoelastics, ointments, pastes, drops (suspension or in solution), nanoparticles, polymeric-based formulations and lotions. The formulations may be applied in any suitable manner, which may include any delivery aid (including but not limited to bandage contact lens, contact lens, formix-based implant, eye patch or patched eye, pressure patch or eye shield, etc.) as deemed appropriate by the human patient or caregiver.

In another embodiment of any embodiment or combination of embodiment herein, the angiotensin peptides may be formulated for slow or sustained release in any suitable manner known I the art. In one embodiment, the peptides are formulated in gel, pellet, nanoparticle, polymeric delivery, cyclodextrin, or any form as a slow or sustained release formulation and placed in the fornix of the conjunctiva for slow or sustained release to the subject.

In another embodiment of all aspects of the invention, the topical formulation comprises about 0.5% to about 4% hydroxyethyl cellulose (HEC) on a weight (mg)/volume (ml) basis, or on a weight/weight (mg) basis. In various further embodiments, the topical formulation may comprise about 1% to about 3% HEC, or about 2% HEC, on a weight (mg)/volume (ml) basis, or on a weight/weight (mg) basis.

In all aspects of the invention, the polypeptides, or salt thereof may be administered together with one or more (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or au acetate buffer. The peptides may be administered with a lyoprotectant, e.g. sucrose, sorbitol or trehalose. In certain embodiments, the peptides may be administered with a preservative e.g. benzalkonium chloride, benzethonium, chlorohexidine phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the peptides may be administered with a hulking agent, like glycine. In yet other embodiments, the peptides may be administered with a surfactant e.g., polysorbate-20, polysorbate-40, polysorbate-60, polysorbate-65, polysorbate-80 polysorbate-85, poloxamer-188, sorbitan monolaurate, sorbitan monopalmitate sorbitan monostearate, sorbitan monooleate, sorbitan trilaurate, sorbitan tristearate, sorbitan trioleate, or a combination thereof. The peptides may be administered with a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the peptides may be administered with a stabilizer, e.g., a molecule which, when combined with the peptide substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride, paraben, and combinations of methyl paraben and propyl paraben.

In all aspects and embodiments of the invention, suitable acids which are capable of forming salts with the polypeptides include, but are not limited to, inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like. Suitable bases capable of forming salts with the peptides include, but are not limited to, inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g., ethanolamine, diethanolamine and the like).

The polypeptides or salts thereof can further be derivatized to provide enhanced half-life, for example, by linking to polyethylene glycol. The peptides or salts thereof may comprise L-amino acids, D-amino acids (which are resistant to L-amino acid-specific proteases in vivo), a combination of D- and L-amino acids, and various "designer" amino acids (e.g. β-methyl amino acids. Cα-methyl amino acids, and Nα-methyl amino acids, etc.) to convey special properties.

The polypeptides may be the sole active agent in the pharmaceutical composition, or the composition may further comprise one or more other active agents suitable for the desired treatment. Such other active agents may include, but are not limited to, one or more of artificial tears (such as Carmellose, Hydroxyethylcellulose, Hypromellose, Polyvinyl alcohol, cyclodextrin), antibiotics (such as Chloramphenicol, Ciprofloxacin, Gentamicin, Neomycin, Polymyxin B) antivirals (such as Acyclovir), antifungals (such as fluconazole), analgesics, and anti-inflammatory drugs (such as non-steroidal anti-inflammatory drugs, topical steroids, cyclosporine and anti-allergy drugs).

Thus, in another aspect, the present invention provides pharmaceutical compositions, comprising:

(a) an angiotensin peptide:

(b) an active agent selected from the group consisting of artificial team (such as Carmellose, Hydroxyethylcellulose, Hypromellose, Polyvinyl alcohol, cyclodextrin), antibiotics (such as Chloramphenicol, Ciprofloxacin, Gentamicin, Neomycin, Polymyxin B), antivirals (such as Acyclovir), antifungals (such as fluconazole), analgesics, and anti-inflammatory drugs (such as non-steroidal anti-inflammatory drugs, topical steroids, cyclosporine and anti-allergy drugs); and (c) a pharmaceutically acceptable carrier.

In one embodiment, the active agent comprises artificial tears (such as Carmellose, Hydroxyethylcellulose, Hypromellose, Polyvinyl alcohol, cyclodextrin). In a further embodiment, the angiotensin peptide comprises or consists of Nle3-A(1-7) (SEQ ID NO: 14).

The angiotensin polypeptide may be present in the pharmaceutical composition in any suitable dose as determined in light of all relevant factors, including those disclosed above for the methods of the invention. The pharmaceutical compositions may be prepared for administration by any suitable route, such as systemic administration (including oral administration); topical administration, including but not limited to as a drop (i.e.: in suspension, in solution, or as an ointment), with a bandage contact lens, sustained delivery via contact lens, a formix-based implant or with an eye patch or patched eye. A topical pharmaceutical composition may comprise, for example, a formulation selected from the group consisting of hydrogels, creams, viscoelastics, ointments, pastes, drops (suspension or in solution), nanoparticles, polymeric-based formulations and lotions. The pharmaceutical compositions may be prepared for administration in any suitable manner, which may include, any delivery aid (including but not limited to bandage contact lens, contact lens, formix-based implant, eye patch or patched eye, pressure patch or eye shield, etc.) as deemed appropriate by the human patient or caregiver. In one embodiment, the pharmaceutical composition comprises a topical formulation comprising about 0.5% to about 4% hydroxyethyl cellulose (HEC) on a weight (mg)/Volume (ml) basis, or on a weight/weight (mg) basis. In various further embodiments, the topical formulation may comprise about 1% to about 3% HEC, or about 2% HEC, on a weight (mg)/volume (ml) basis, or on a weight/weight (mg) basis.

The pharmaceutical formulation may comprise one or more (a) a lyoprotectant; (h) a surfactant; (c) a bulking agent; (d) a tonicity adjusting agent; (e) a stabilizer; (f) a preservative and/or (e) a buffer, such as those described herein for the methods of the invention.

The methods may be used in conjunction with other therapies suitable for treating the relevant disorder.

The methods and compositions may include any other embodiments as disclosed in the example that follows. Such embodiments may be used in any combination in the methods of the invention, unless the context clearly dictates otherwise.

Example 1

Corneal healing is important, not only to reestablish the protective epithelium, but also for the restoration of corneal transparency and clear vision. The corneal healing response depends on various factors including the type, size, and extent of the wound; the nature of the injuring agent; the status of the eye; and the general status of the subject. The most common corneal injuries involve superficial penetration of the epithelium, Bowman's membrane, and the anterior part of the stroma. Superficial corneal defects may be associated with trauma or diseases, such as dystrophies, neurotrophic, toxic, or infective keratitis, but also follow surgical procedures such as epithelial debridement, phototherapeutic keratectomy, photorefractive keratectomy, or laser in situ keratomilensis. In all these cases, regardless of the etiology, the main therapeutic goal is to promote structural restoration with minimal scarring to provide the best possible optical outcome. Various mechanisms for corneal healing have been hypothesized and described including the role of different growth factors, their regulators, and receptors. Regardless of the depth of the injury, it appears that keratocytes are always involved in the process of healing and the challenge remains to promote healing via regeneration not fibrosis. Due to its exposed site and sheerness, corneal surface injuries are the most common ophthalmic, complaint and recurrent erosions develop in a sub-population of patients with surface injuries. The purpose of this study is to evaluate the effects of a new topical drug on corneal re-epithelialization and stromal wound healing.

Animal Preparation and Procedure:

Before each procedure, the rabbits were anesthetized with a subcutaneous injection of a mixture of ketamine hydrochloride (50-80 mg/kg) and xylazine hydrochloride (5-9 mg/kg). The animal was prepared for sterile surgery conducted under aseptic conditions. Periorbital area was cleaned using 5% povidone iodine solution and a drop of this solution was instilled into the fornix and a speculum was used to hold the eyelids open. Using corneal blade (Keratome 3.2 mm), a clear corneal full-thickness tunnel was created in the same manner as in human phacoemulsification surgery. To prevent the globe collapse after corneal tunnel creation, a small amount of viscoelastic was injected in the anterior chamber through a paracentesis. Gentamicin 25 mg, and dexamethasone 2 mg were injected subconjunctivally. Post-operatively, analgesia was administered. Animals allocated to the treatment group were treated with 1 drop (approximately 50 µl) of the active drug (0.03% or 0.3% Nle3 A(1-7) in 2% hydroxyethyl cellulose in 0.05 M phosphate buffer, pH 6.5) under investigation instilled into the conjunctival sac daily (using a dropper throughout the follow-up period. On the other hand, animals allocated to the control group will be treated with vehicle (2% hydroxyethyl cellulose in 0.05 M phosphate buffer, pH 6.5) eyedrops daily throughout the follow-up period.

Follow-up Examination:

These ocular follow-up examinations were done while the animal was under anesthesia as described above. Anterior segment imaging includes red free picture and anterior segment fluorescein imaging using Spectralis (Heildelberg Engineering, Germany) where sequential photos are taken after one drop of 10% fluorescein (Akorn Abit Springs, La.) was instilled in the conjunctival sac and a slight pressure was applied to the globe. This is more commonly known as Seidel's test in which fluorescein strip containing 10% fluorescein was applied topically to the affected area and was examined with a cobalt blue filter. At this point, the fluorescein appears green in color. Any changes in color or surface of the fluorescence area indicate the presence of conical leakage. This imaging data were used to assess the degree of corneal wound healing as well as extent of wound leak. Measurement of the intraocular pressure was performed using Tonopen-AVIVA (TPA, Reichert Inc.).

Imaging and Histology:

The injury was also imaged using involved using a Heidelberg Retina Tomograph (HRT) instrument. This is a confocal scanning laser ophthalmoscope which was converted into a confocal corneal microscope using an additional microscope lens which attached to the standard lens. This additional lens enabled the HRT to image cells and cell layers within the cornea to allow an in-life phase assessment of the healing and structure of the cornea to allow detailed views of the conical structure and pathology.

Results

In the rabbit model of full thickness injury, application of Nle3-A(1-7) daily to the eye reduced the time to conical healing as defined by no leakage on the Seidel's test from 7 days in the vehicle treated animals to 4 days in all animals treated with active drag (both concentrations). Further, there was a reduction in the inflammation/edema in the eye measures by clinical observation. When the animals were treated with vehicle, inflammation/edema continued to be moderate at day 7. With treatment with the lower concentration of Nle3 A(1-7) (0.03%), the edema was very mild on day 7 With treatment with the higher concentration of drug (0.3%), edema was observed only for the first 5 days after surgery. This shows a unique capability to both reduce inflammation and accelerate corneal healing by this active compound. This was accompanied by no change in intraocular pressure as well as a normal fundus examination and fluorescein angiography.

| Eyedrops | Seidel's Test (for wound leakage) | Corneal Wound Edema | IOP | Fundus Exam & Fluorescein angiography | Complications |
| --- | --- | --- | --- | --- | --- |
| $Nle^3$-A(1-7) 0.3% | Leakage on the $1^{st}$ 3 days No leakage from the $4^{th}$ day | Persisted for the $1^{st}$ 5 days only | Normal | Normal | None |
| $Nle^3$-A(1-7) 0.03% | Leakage on the $1^{st}$ 3 days No leakage from the day-4 | Mild at day 7, but diminishing. | Normal | Normal | None |

-continued

| Eyedrops | Seidel's Test (for wound leakage) | Corneal Wound Edema | IOP | Fundus Exam & Fluorescein angiography | Complications |
|---|---|---|---|---|---|
| Vehicle | Leakage for the 1st 6 days No leakage from the 7th day | Moderate at day 7, but diminishing | Normal | Normal | None |

Evaluation of the site of incision by HRT and histological evaluation was also conducted (Day 10). In the vehicle treated animals, there was fibrosis and disruption of normal corneal architecture at the site of incision. A representative example of this observation can be seen in the HRT images below. At the site of incision in the vehicle treated eye, there is a deposition of a large amount of fibrous material that disrupts the corneal architecture. With treatment with Nle3-A(1-7) the wound was healed and the tissue has a normal appearance and architecture. This was further demonstrated at necropsy (day 21), when tissues were harvested and prepared for microscopic evaluation. Hematoxylin and eosin staining of the incision site showed normalized architecture with reduced fibrosis with active treatment (FIG. 1).

Application of 0.3% and 0.03% Nle3-A(1-7) following full-thickness corneal incision resulted in faster resolution of edema and inflammation, reduction in the duration of conical wound leakage, and healing with normal architecture and no fibrosis compared to vehicle control animals. The higher concentration, 0.3% Nle3-A(1-7), had the shortest duration of edema and inflammation, all other parameters were equal between the two Nle3-A(1-7) arms.

Example 2

Principle of test: Determine effect of Nle3-A(1-7) in vehicle (2% hydroxyethyl cellulose (HEC) in 0.05 M phosphate buffer, pH 6.5) on corneal healing, determined by oblique light exam. Seidel's test, confocal microscopy and in vivo leakage pressure, following full-thickness conical incision in rabbit.

Animals:

Male and female, pigmented rabbits, right eye only, 5/group, weighing 5-6 lbs. The rabbits were anesthetized with a subcutaneous injection of a mixture of ketamine hydrochloride (50-80 mg/kg) and xylazine hydrochloride (5-9 mg/kg). The animals were prepared for sterile surgery conducted under aseptic conditions. The periorbital area was cleaned using 5% povidone iodine solution and a drop of this solution was instilled into the fornix. A speculum was used to hold the eyelid open. Using a corneal blade (Heratome 3.2 mm), a clear corneal nil-thickness incision was created. Post-operatively, analgesia was administered followed by test article. Approximately 30 minutes to an hour later antibiotic ointment was administered.

Test and Reference Substances and Treatment Schedule:

TABLE 1

| Group | Treatment Arm | Route | Schedule | Duration | Notes |
|---|---|---|---|---|---|
| 1 | 0.3% Nle3-A(1-7)in vehicle | Conjunctival | OD | 28 days | Right eye |
| 2 | 0.03% Nle3-A(1-7)in vehicle | Conjunctival | OD | 28 days | Right eye |
| 3 | Vehicle control | Conjunctival | OD | 28 days | Right eye |

Evaluations:

TABLE 2

| Test | Timing (Day) | Details |
|---|---|---|
| Oblique light examination | 2, 4, 6, 8, 10, 12, 14, 21, 28 | Observation for edema, gross findings and anterior chamber formation |
| Seidel's test with slit lamp examination | 5, 10 | 10% fluorescein strip applied to affected area while pressure is applied, leakage of aqueous fluid through the incision results in a color change |
| In vivo leakage pressure measurement | 7 | 3 animals per group, intraocular pressure is increase in 10 mmHg increments, measured by Constellation Vitrectomy machine, to determine pressure at which the incision leaks |
| Confocal microscopy imaging | 28 | Heidelberg Retina Tomograph (HRT) for detailed in-life views of the corneal structure and pathology |
| Sample collection | 28 | Future analyses to include hematoxylin and eosin stained sections by light microscopy, scanning electron microscopy and immunohistochemical staining |

Results:

Oblique Light Examination:

All animals had conjunctival discharge or severely congested eyes on Day 2. On Day 4 discharge was limited to 1 animal at 0.3% Nle3-A(1-7), 1 at 0.03% Nle3-A(1-7), and 2 vehicle-treated eyes. Anterior chamber (AC) formation is first noted on Day 4 in the 0.3% group with all 5 high dose animals having fully formed AC on Day 6. In the 0.03% group 4 of the 5 animals had full AC on Day 6, with the remaining animal having fully formed AC on Day 8. The first record of 100% AC formation in the vehicle group was on Day 12, with all AC complete on Day 14 (Week 2).

Seidel's Test:

All animals had positive Seidel's test results on Day 5 with the exception of 3 animals. 2 at 0.3% Nle3-A(1-7) and 1 at 0.03% Nle3-A(1-7). On Day 10 all Nle3-A(1-7)-treated animals had negative Seidel's tests, while all vehicle-treated animals continued to have leakage with pressure. Further, the oblique light exam on Day 6 found no observed leakage in any animal in the 0.3% NorLeu$^3$-A(1-7) group and none in three, animals in the 0.03% Nle3-A(1-7) group.

In Vivo Leakage Pressure:

Three animals from each treatment group had in vivo pressure measurements taken. The mean pressure for animals receiving 0.3% or 0.03% Nle3-A(1-7) was 79.3±6 mmHg and 77.3±3.2 mmHg respectively. The mean pressure for vehicle-treated animals was 38.7±3.2 mmHg. Treatment, with Nle3-A(1-7) increased the strength, of healing in that it took approximately twice the amount of pressure to cause leakage in Nle3-A(1-7)-treated wounds compared with vehicle-treated wounds.

Figure 2:
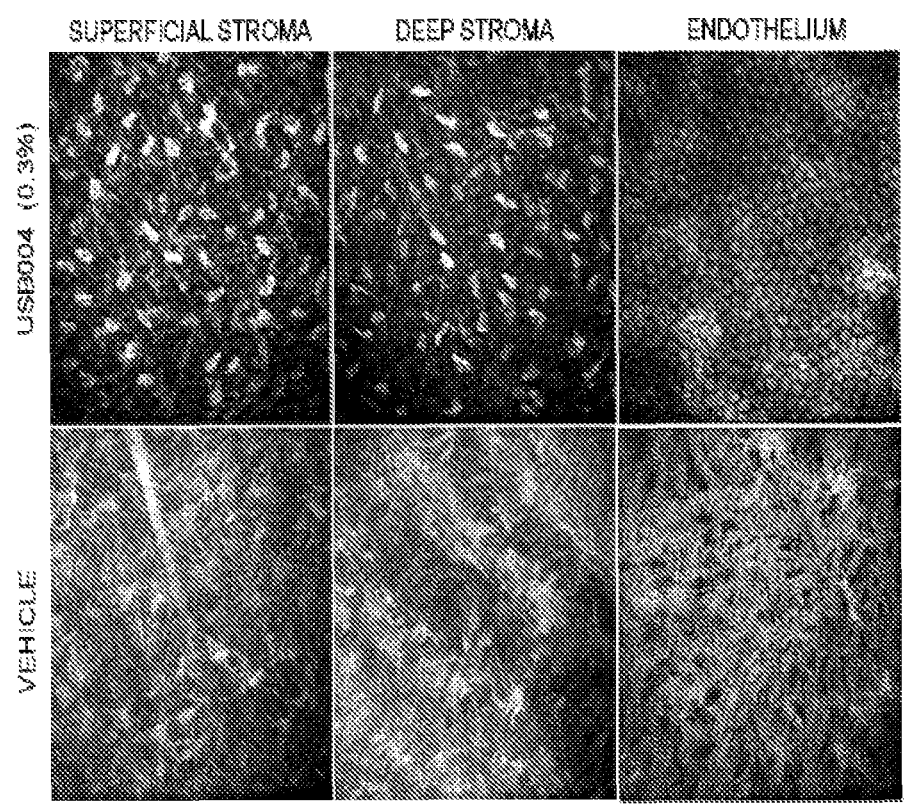
FIG. 2. Confocal microscopy imaging, shows regular arrangement of the collagen stromal lamellae in the vicinity of the conical wound in the two Nle3-A(1-7) treatment groups, as compared with the rough and haphazard arrangement seen in the vehicle group after 1 month of daily treatment.

Confocal microscopy (FIG. 2): Shows regular arrangement of the collagen stromal lamellae in the vicinity of the corneal wound in the two Nle3-A(1-7) treatment groups, as compared with the rough and haphazard arrangement seen in the vehicle group after 1 month of daily treatment.

DISCUSSION AND CONCLUSIONS

Application of 0.3% and 0.03% Nle3-A(1-7) following full-thickness conical incision resulted in faster anterior chamber formation compared to vehicle control animals, Day 6, Day 8 and Day 14 respectively. Corneal healing, measured by aqueous leakage in the Seidel's test, occurred by Day 10 in all Nle3-A(1-7)-treated animals with no vehicle control animals having a negative Seidel's test.

The strength of healing was increased following 0.3% and 0.03% Nle3-A(1-7) treatment compared to vehicle control animals. Regular distribution of the keratocytes and lamellae indicate corneal healing in the Nle3-A(1-7)-treated animals.

We claim:

1. A method for treating an eye injury, comprising administering to a subject with an eye injury an amount effective of a peptide comprising Nle3-A(1-7) (SEQ ID NO: 14) to treat the eye injury.

2. The method of claim 1, wherein the eye injury is caused by trauma, light/radiation or chemical exposure, disease, or a surgical procedure.

3. The method of claim 1, wherein the eye injury comprises an injury selected from the group consisting of post-surgical inflammation, postoperative fibrosis, a post-surgical increase in intra-ocular pressure, a corneal injury, a cataract incision, laser-assisted in situ keratomileusis (LASIK) wounds, dry eye, and a photorefractive keratectomy (PRK) wound.

4. The method of claim 1, wherein the eye injury is a corneal injury, and wherein the corneal injury comprises penetration of the corneal epithelium, corneal endothelium, corneal Bowman's membrane, Descemet's membrane and/or anterior part of the corneal stroma, or wherein the corneal injury comprises a corneal abrasion or corneal laceration.

5. The method of claim 4 wherein the treating comprises one or more of (a) reduced time to corneal healing and/or anterior chamber formation compared to control, and (b) reducing development and/or severity of a symptom selected from the group consisting of fibrosis, inflammation, edema, increases in intraocular pressure, eye pain, increased tearing compared to normal, blurred vision, sensitivity to light, altered visual acuity, and a sensation of something being stuck in the eye.

6. The method of claim 1 wherein the eye injury comprises dry eye.

7. The method of claim 4, wherein the treating comprises reducing development and/or severity of a symptom selected from the group consisting of eye irritation, stinging, redness, grittiness, scratchiness, burning, conjunctival discharge, a feeling of something in the eyes, excess watering, and blurred vision.

8. The method of claim 1 wherein the eye injury results from ocular surgery.

9. The method of claim 8, wherein the ocular surgery is selected from the group consisting of keratomilleusis, laser-assisted in situ keratomilleusis (LASIK), automated lamellar keratoplasty (ALK), laser assisted sub-epithelial keratomileusis (LASEK), photorefractive keratectomy (PRK), laser thermal keratoplasty (LTK), conductive keratoplasty (CK), limbal relaxing incisions (LRI), astigmatic keratotomy (AK), radial keratotomy (RK), mini-asymmetric radial keratotomy (M.A.R.K.), hexagonal keratotomy (HK), implantable contact lenses, presbyopia reversal, anterior ciliary sclerotomy (ACS), laser reversal of presbyopia (LRP), scleral expansion bands, the Karmra inlay, scleral reinforcement surgery, corneal transplant surgery, penetrating keratoplasty (PK), keratoprosthesis implantation (KPro), cataract surgery, insertion of intra-ocular lenses, phototherapeutic keratectomy (PTK), pterygium excision, corneal tattooing, vitrectomy, pan retinal photocoagulation (PRP), retinal detachment repair, laser photocoagulation, pneumatic retinopexy, retinal cryopexy, macular hole repair, partial lamellar sclerouvectomy, partial lamellar sclerocyclochoroidectomy, partial lamellar sclerochoroidectomy, posterior sclerotomy, radial optic neurotomy, macular translocation surgery, eye muscle surgery, oculoplastic surgery, and surgery to treat cataracts, glaucoma, and diabetic retinopathy.

10. The method of claim 1, wherein the treating comprises reducing development and/or severity of a symptom selected from the group consisting of postoperative fibrosis, postoperative inflammation, postoperative increases in intraocular pressure, lacerations, conjunctival discharge, punctures, eye pain, increased tearing compared to normal, blurred vision, sensitivity to light, altered visual acuity, and a sensation of something being stuck in the eye.

11. The method of claim 1, wherein the peptide consists of Nle3-A(1-7) (SEQ ID NO: 14).

12. The method of claim 1, wherein the peptide is administered at a concentration of about 0.01% to about 1% on a weight (mg)/volume (ml) basis, or on a weight/weight (mg) basis.

13. The method of claim 1, wherein the peptide is administered in a topical formulation.

14. The method of claim 13, wherein the topical formulation is selected from the group consisting of hydrogels, creams, viscoelastics, ointments, pastes, drops, nanoparticles, polymeric-based formulations and lotions.

15. The method of claim 13, wherein the formulation is administered via a delivery aid selected from the group consisting of a bandage contact lens, contact lens, formix-based implant, eye patch or patched eye, pressure patch, and eye shield.

16. The method of claim 13, wherein the topical formulation comprises about 0.5% to about 4% hydroxyethyl cellulose (HEC) on a weight (mg)/volume (ml) basis, or on a weight/weight (mg) basis.

17. The method of claim 1, wherein the method further comprises administering to the subject an amount effective to treat an eye injury of an active agent selected from the group consisting of artificial tears, antibiotics, antivirals, antifungals, analgesics, and anti-inflammatory drugs.

* * * * *